United States Patent [19]

Finkelstein

[11] Patent Number: 4,797,359

[45] Date of Patent: Jan. 10, 1989

[54] HEAT SHOCK REGULATED PRODUCTION OF SELECTED AND FUSED PROTEINS IN YEAST

[75] Inventor: David B. Finkelstein, Dallas, Tex.
[73] Assignee: Board of Regents, The University of Texas System, Austin, Tex.
[21] Appl. No.: 493,251
[22] Filed: May 10, 1983
[51] Int. Cl.$^4$ .................. C12P 21/00; C12P 21/02; C12N 5/00; C07H 15/12
[52] U.S. Cl. .................................. 435/68; 435/70; 435/172.3; 435/255; 435/256; 435/320; 536/27; 935/28; 935/37; 935/43; 935/47; 935/69
[58] Field of Search .................. 435/68, 172.3, 224, 435/255, 256, 260, 317, 70, 320; 935/28, 37, 43, 47, 69, 111; 536/27

[56] References Cited

U.S. PATENT DOCUMENTS 4,374,927 2/1983 Sninsky .............................. 435/68

OTHER PUBLICATIONS

Cover pages–Heat Shock, From Bacteriato Man, Cold Spring Harbor Laboratory 1982.
Finkelstein, D. B. and Strausberg, S. (1982), "Expression of a Cloned Yeast Heat Shock Gene," (Abstract handed out to Cold Spring Harbor Conf. attendants on May 5, 1982).
Nasmyth, K. A. and Tatchell, K. (1980), "The Structure of Transposable Yeast Mating Type Loci" *Cell*, 19:753–764.
Integration, Transcription, and Control of a Drosophila Heat Shock Gene in Mouse Cells; Proc. Natl. Acad. Sci. vol. 78, No. 11, pgs. 7038–7042 by Corces, Pellicer et al.; Nov. 17/81.
Approximate Localization of Sequences Controlling Transcription of a Drosophila Heat-shock Gene; Heat Shock From Bacteria to Man, pp. 27–34, May 5–9, 1982 by Corces, Pellicer et al.
Transcription and Chromatic Structure of Drosophila Heat-shock Genes in Yeast; by Lis, Costlow et al., Heat Shock pp. 57–62, 1982.
Altered Patterns of Protein Synthesis Induced by Heat Shock of Yeast; by McAlister, Strausberg et al., Current Genetics 1 Jun. 28, 1979 pp. 63–74.
Heat Shock Proteins and Thermal Resistance in Yeast; Biochemical and Biophysical Research Communications vol. 93 No. 3 by McAlister and Finkelstein, 2/26/80, pp. 819–824.
Alterations in Translatable Ribonucleic Acid After Heat Shock of *Saccharomyces cerecisiae;* J. of Bacteriology vol. 143 No. 2 pp. 603–612 by McAlister and Finkelstein; Aug. 1980.
Alterations of Transcription During Heat Shock of *Saccharomyces cerevisiae;* J. of Biological Chemistry vol. 257 No. 14, pp. 8405–8411 by Finkelstein, Strausberg et al.; 7/25/82.
Expression of a Cloned Yeast Heat-shock Gene; by Finkelstein and Strausberg, Heat Shock From Bacteria to Man, 1982, pp. 63–68.
Identification and Expression of a Cloned Yeast Heat Shock Gene; by Finkelstein and Strausberg; J. of Biological Chemistry, vol. 258 No. 3 Feb. 10, 1983 pp. 1908–1913.
Yeast Genes Fused to B-galactosidase in *Escherichia coli* Can Be Expressed Normally in Yeast; Proc. Natl. Acad. Sci. vol. 78 No. 4 pp. 2460–2464 by Rose, Casadaban et al.; Apr. '81.
Fusion of *Escherichia coli* lacZ to the Cytochrome C Gene of *Saccharomyces cerecisiae;* Proc. Natl. Acad. Sci. vol 78, No. 4 pp. 2199–2203 by Guarente and Ptashne; Apr. '81.
Expression of a Human Gene for Interferon in Yeast; by Hitzeman, Hagie et al.; Oct. 29, 1981 Nature vol. 293, pp. 717–722.
Synthesis and Assembly of Hepatitis B Virus Surface Antigen Particles in Yeast; Valenzuela, Medina et al.; Nature vol. 298, pp. 347–350. Jul. 22, 1982.

*Primary Examiner*—Thomas G. Wiseman
*Assistant Examiner*—Robin Lyn Teskin
*Attorney, Agent, or Firm*—Arnold, White & Durkee

[57] ABSTRACT

A process for producing a yeast capable of heat regulated synthesis of selected and fused proteins is disclosed. The process involves the combination of a DNA fragment comprising a heat shock inducible gene of an appropriate yeast microorganism and a second DNA fragment comprising a selected gene with a suitable transfer vector, thereby producing a recombinant transfer vector. A suitable host yeast is contacted with the recombinant transfer vector, cultured and transformants having the desired genetic capability are selected.

15 Claims, 3 Drawing Sheets

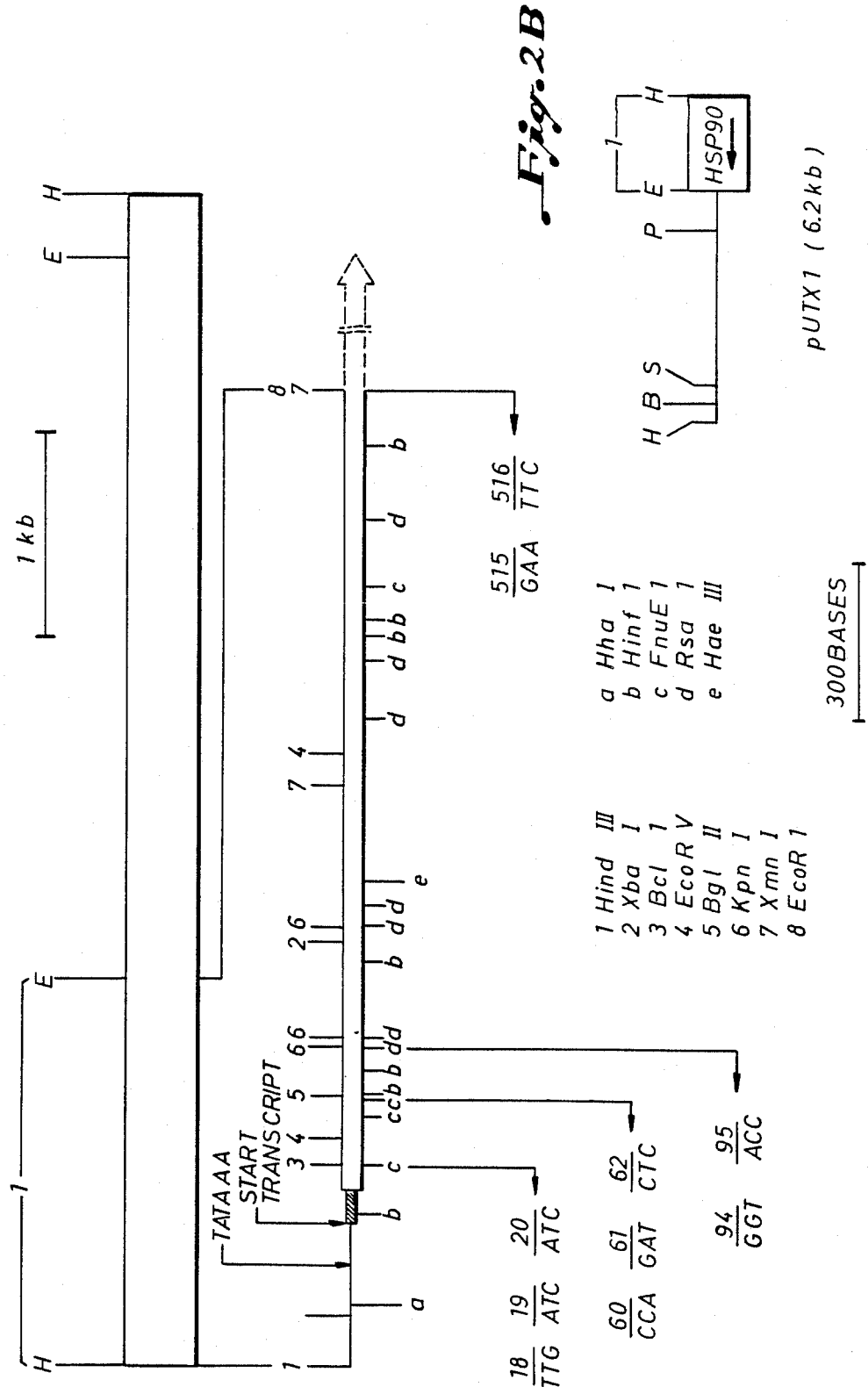

HEAT SHOCK REGULATED PRODUCTION OF SELECTED AND FUSED PROTEINS IN YEAST

BACKGROUND OF THE INVENTION

This invention relates to a process for producing yeast capable of heat-regulated synthesis of selected and fused proteins. More particularly, this invention relates to a process for cloning selected genes coupled to yeast heat shock inducible genes to produce yeast capable of heat-regulated synthesis of selected and fused proteins.

By the use of recombinant DNA technology it is, in principle, possible to introduce any given DNA sequence into an organism. The method for achieving such a DNA transfer generally employs a procedure which joins the selected DNA to a suitable DNA molecule which may be introduced into the desired organism by transformation. The suitable DNA (termed transfer vector) will contain sequences which allow for the selection of transformants by being able to correct a particular genetic defect in the host organism or by providing resistance to certain drugs. Additionally, the suitable DNA contains sequences which allow this molecule to replicate autonomously in the desired organism or to be integrated into one (or more) of the chromosomes of the desired organism.

If the given DNA sequence encodes a given protein, in order for this protein to be expressed in an organism a number of events must first occur. The DNA sequence must be transcribed by the recipient organism to give rise to an RNA molecule which contains all of the protein coding sequences. This RNA transcript must then attach to the ribosomes of the recipient cell in order for translation to occur. In order for the protein to be properly translated, translation must begin exactly at the nucleotide sequence which encodes the initiation of protein synthesis. Once this has occurred, the universality of the genetic code will allow protein synthesis to proceed to synthesize the desired protein product.

While the genetic code is universal, the DNA sequences which control the site of transcription origin and the regulation of this transcription (termed regulatory sequences or promotor sequences) are specific for given genes in a given organism. Therefore, the sequences which regulate transcription in one organism may not have this function in another organism. Furthermore, the efficiency with which a given RNA is translated contains organism-specific sequences as well. Thus, merely because a DNA sequence is transcribed to give rise to an RNA, this by no means ensures that this RNA will be properly translated. The position of the sequence encoding the origin of translation must be appropriately situated relative to the ends of the RNA molecule in order for translation to give rise to the proper protein product.

To allow for the expression of a given selected DNA sequence in a desired host organism, the regulatory sequences and sequences necessary for ribosome binding obtained from a gene known to function in the host organism must be placed in appropriate position relative to the selected DNA sequence. If the gene fusion is such that only coding sequences of the selected DNA are utilized, the result may be the production of the selected protein. If the fusion is such that in addition to the promoter sequences and ribosome binding sites a portion of the coding sequence for the host cell protein is placed adjacent to the coding sequence for the selected protein (and the fusion is such that the translational reading frame established by the "upstream" host protein sequences is the same as that employed by the "downstream" selected protein coding sequences), the result is a fused protein whose amino end consists of host protein and whose carboxyl end consists of selected protein.

Commercially valuable proteins, such as enzymes, hormones, and proteins utilized in the production of vaccines, may be synthesized in yeast cells which have been modified by recombinant DNA technology as described above. See Hitzemen et al., "Expression of a Human Gene for Interferon in Yeast," Nature 293, 713 (1981); Valenzuela et al., "Synthesis and Assembly of Hepatitis B Virus Surface Antigen Particles in Yeast," Nature 298, 347 (1982). The economic value of such genetic engineering is substantial as yeast may be propagated rapidly and cultured in large scale fermentors.

Current methods for the regulation of gene expression and protein synthesis within genetically modified yeast cells require a change in the nutritional status of the culture medium, such as the addition or removal of a particular nutrient. For example, utilization of the inducible yeast phosphatase gene to regulate the expression of a selected gene requires that cultures have low levels of inorganic phosphate as the gene is unexpressed in the presence of high levels of inorganic phosphate. Therefore, regulating the synthesis of a selected protein using the inducible yeast phosphatase gene requires an appropriate means to remove phosphate from the growth medium. Such a nutritional change in the culture medium is impractical. Alternatively, the gene for galactokinase may be employed to allow regulated expression of a selected gene. In this instance, glucose must be absent from the growth medium and gene expression is initiated upon addition of galactose. However, this method is very costly as galactose is an expensive substrate. Alternatively, the genes encoding for a number of enzymes of glycolysis may be employed to allow the expression of selected genes in yeast. However, this method is also impractical as these genes are not readily regulated. Thus, where regulated expression in yeast can occur, it requires an impractical or expensive alteration in the nutritional status of the culture medium, considerably diminishing the value of synthesizing desirable proteins within yeast.

The present invention overcomes the limitations discussed above by utilizing heat shock inducible genes of an appropriate yeast microorganism. Expression of heat shock inducible genes may be induced merely by raising the cultivation temperature of the yeast microorganism. Thus, the manipulation of temperature elevation will induce the synthesis of yeast heat shock proteins when the yeast organism is cultivated in any medium which allows cell growth. Furthermore, the heat shock response, elicited by a shift in the cultivation temperature beyond a critical level, results in a dramatic alteration of cellular transcription and ultimately in an increased level synthesis of heat shock protein. See, McAlister et al., "Altered Patterns of Protein Synthesis Induced by Heat Shock of Yeast," Current Genetics 1, 63 (1979).

Accordingly, the present invention provides a means for heat-regulated expression of a selected gene in a host yeast by fusion of the selected gene with the regulatory sequence of a yeast heat shock inducible gene. Thus, the point in cultivation where selected and fused proteins are synthesized may be controlled by a simple thermal shift. Further, fusion of a selected gene to the regulatory sequence of the heat shock inducible gene permits a high level of production of selected and fused proteins in a yeast host for the duration of the heat shock response.

SUMMARY OF THE INVENTION

In its broadest scope, the present invention provides a process for producing a transformed yeast microorganism capable of heat-regulated synthesis of a selected protein or portion thereof. Alternatively, the present invention provides a process for producing a transformed yeast microorganism capable of heat-regulated synthesis of a stable fused heat shock protein and a selected protein or portion thereof.

To perform the processes of this invention, DNA containing a heat shock inducible gene region of an appropriate yeast microorganism is isolated. The preferred means of isolating the desired DNA is by selection from recombinant DNA libraries. The preferred yeast microorganism is S.cerevisiae, having the HSP90 gene region. The DNA containing the heat shock inducible gene region is thereafter digested by suitable restriction procedures to produce a DNA fragment comprising the heat shock inducible gene, including the regulatory sequence of the gene.

By well known recombinant DNA techniques, a recombinant transfer vector is prepared by combining a suitable transfer vector or portion thereof with the DNA fragment described above and a second DNA fragment containing a DNA sequence encoding for synthesis of a selected protein or portion thereof. The selected gene of the second DNA fragment may originate from the host yeast microorganism or may be foreign to the host microorganism, the preferred gene being the lacZ gene of E. coli encoding for $\beta$-galactosidase synthesis.

If fusion of the DNA fragments described above includes the regulatory sequence of the heat shock inducible gene, but does not include the DNA sequences encoding for synthesis of the heat shock protein or a portion thereof, the resultant gene product will be the selected protein. Alternatively, if fusion of the DNA fragments includes coding sequences of the heat shock inducible gene in addition to the regulatory sequence with the point of fusion being located within the coding sequences of the heat shock inducible gene and within or upstream from the coding sequences of the selected gene such that the translational reading frames are compatible, the resultant gene produce will be a fused protein. Further, the resultant gene product will be a biologically active protein comprising the heat shock protein or portion thereof and the selected protein or portion thereof.

The recombinant transfer vector of the present invention may be a plasmid DNA or an other DNA sequence which allows for its replication and selection upon introduction in a suitable host yeast microorganism. The preferred recombinant transfer vector of the present invention, pUTX41, is derived from the plasmid pUTX37, and comprises the combination of a DNA fragment having the HSP90 regulatory sequence and a DNA fragment having coding sequences for $\beta$-galactosidase synthesis.

The recombinant transfer vector containing the desired genetic material is thereafter introduced into a host yeast microorganism, such as S.cerevisiae, by the process of transformation. The transformed host microorganism is then cultured in a suitable culture medium and transformants having the desired genetic capability are selected by appropriate selection techniques.

The present invention is also directed to a transformed host yeast microorganism, transformed by the recombinant transfer vector of this invention and produced by the processes as described above. Accordingly, a host yeast is transformed so as to be capable of the heat-regulated synthesis of a selected protein or portion thereof. Also in accordance with the present invention, a host yeast is transformed so as to be capable of heat-regulated synthesis of a stable fused heat shock protein and selected protein or portion thereof.

The present invention is further directed to a process for the heat-regulated synthesis of a selected protein or a portion thereof, or a stable fused heat shock protein and selected protein or portion thereof, within a yeast microorganism. The process comprises culturing a transformed yeast microorganism of the present invention having the desired genetic capability.

This invention is predicated upon the use of a heat shock inducible gene to regulate the expression of a selected gene or portion thereof by temperature control. Expression of heat shock inducible genes may be induced merely by a shift in the cultivation temperature of the host yeast microorganism. Accordingly, the synthesis of selected and fused proteins within a host yeast may be heat-regulated by coupling a selected gene to the regulatory sequence of a heat shock inducible gene, such as HSP90.

In S.cerevisiae, a shift in the cultivation temperature from 23° to 36° induces expression of the HSP90 gene and results in the hsp90 protein being the most abundantly synthesized cellular protein for the duration of the heat shock response. Accordingly, fusion of the HSP90 regulatory sequence to a selected gene permits a high level of synthesis of selected and fused proteins within a host yeast for the duration that the hsp90 protein would be overproduced.

The present invention is of significant utility as it provides an effective and efficient means for the heat-regulated synthesis of desired proteins as well as stable fused proteins. Thus, the production of commercially valuable proteins, such as hormones, enzymes, and proteins utilized in the production of vaccines, may be regulated by a simple thermal shift in the cultivation temperature. Additionally, the capability of regulating the synthesis of a desired protein or a stable fused protein by a thermal shift, makes it possible to regulate the synthesis of a secondary metabolite of commercial importance, produced as a result of the altered yeast metabolism.

Examples of the more important features of this invention have thus been summarized rather broadly in order that the detailed description thereof that follows maybe better understood, and in order that the contribution to the art may be better appreciated. There are, of course, additional features of the invention that will be described hereinafter and which will also form the subject of the claims appended hereto.

BRIEF DESCRIPTION OF THE DRAWINGS

FIG. 1 also shows the presence of a 2.2 kilobase pair region (marked 2μ) which contains the replication origin of the S.cerevisiae 2 plasmid DNA. FIG. 1 also shows the 2.2 kilobase segment which contains the *S.cerevisiae* LEU2 gene region.

FIG. 2A shows a DNA fragment of *S. cerevisiae*, having a molecular length of 5.6 kilobase pairs and containing the HSP90 gene. FIG. 2A also shows the region encoding the hsp90 protein as beginning 332 bases from the leftmost Hind III site.

FIG. 2B shows the plasmid pUTX1 in which the 1.875 kilobase pair Hind III-Eco RI DNA segment of the yeast HSP90 gene is placed in pBR322 between the Hind III and Eco RI sites.

DETAILED DESCRIPTION OF THE INVENTION

Figure 1:
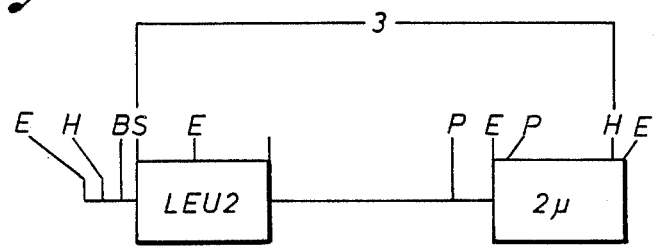
FIG. 1 shows a linear representation of the circular transfer vector pUTX37, having a molecular length of 8.8 kilobase pairs, with Hind III(H), Sal I(S), Bam I(B), Pst(P) and Eco RI(E) restriction sites.
Figure 3:
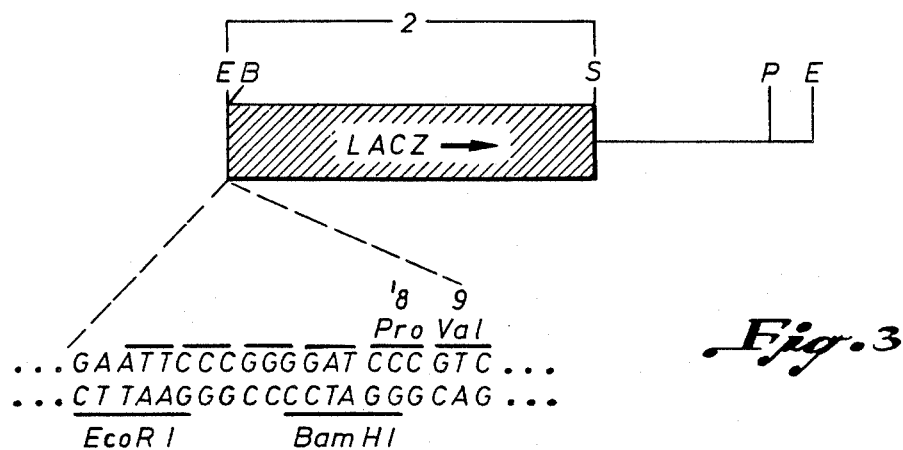
FIG. 3 shows plasmid pMC1403 of *E.coli* which contains a 6.2 kilobase pair fragment encoding the 5'deleted lacZ gene to which linkers suitable for fusion have been attached. The reading frame required for correct translation of lacZ is indicated.

In accordance with the present invention, DNA containing a heat shock inducible gene region of an appropriate yeast microorganism is isolated and purified. The preferred yeast microorganism is *S.cerevisiae* having the preferred heat shock inducible gene HSP90. The preferred means of isolating the HSP90 gene is by selection from the recombinant DNA libraries, λCharon 4- *S.cerevisiae* and YEp13-*S. cerevisiae*, containing yeast DNA segments inserted into appropriate plasmid phage or plasmid molecules. Isolation and purification of the desired DNA is accomplished essentially as described by Finkelstein et al., *J. Biol. Chem.* 257, 3405 (1982), which is herein incorporated by reference.

Once the plasmid DNA containing the yeast HSP90 gene region is isolated and purified, it is then digested by appropriate restriction procedures to obtain a DNA fragment comprising the heat shock inducible gene HSP90, including the HSP90 regulatory sequence. The desired DNA fragment may be characterized as a 1.875 kilobase Hind III - Eco RI fragment, including DNA sequences regulating expression of the HSP90 gene as well as sequences encoding the first 516 amino acid residues of the hsp90 protein. Restriction endonucleases Hind III and Eco RI are utilized to obtain the the Hind III - Eco RI fragment as described above because of their capability of catalyzing site-specific cleavage of the Hind III and Eco RI restriction sites. This fragment may thereafter be introduced into pBR322 to produce plasmid pUTX1 for the purposes of effective gene manipulation and reisolation of the fragment (see FIG. 2B).

A recombinant transfer vector is thereafter prepared in accordance with standard recombinant techniques by combining a suitable transfer vector or portion thereof with the DNA fragment described above and a second DNA fragment comprising the lac Z gene of *E.coli* encoding for β-galactosidase synthesis. The second DNA fragment comprising a 6.2 kilobase Eco RI - Sal I fragment, is excised from the commonly available plasmid pMC1403. In accordance with standard procedures, this fragment is obtained by digestion of pMC1403 with Eco RI and Sal I restriction endonucleases. Further, this fragment may be characterized as containing the sequences which encode all but the first 8 amino acid residues of the *E.coli* β-galactosidase protein and includes 16 extra nucleotides (ending with the Eco RI site) at the 5' end of the DNA segment to allow linkage to another DNA segment via ligation of the common Eco RI generated cohesive ends (See FIG. 2C). While the lac Z gene is the preferred gene for recombination with yeast heat shock inducible genes, it is recognized that other desired genes, both originating from the host yeast microorganism and foreign to the host yeast, may be suitably utilized in the present invention.

The preferred transfer vector or portion thereof suitable for recombination with the DNA fragments described above so as to produce a recombinant transfer vector is an 8 kilobase Hind III - Sal I fragment derived from plasmid pUTX37. Plasmid pUTX37, constructed in this laboratory, is equivalent to plasmid CV7, described by Broach, J. R. and Hicks, J. B., "Replication and Recombination Functions Associated with the Yeast Plasmid, 2μ circle," *Cell* 21:501 (1980), which is herein incorporated by reference. Additionally, the preferred transfer vector contains DNA replication origins capable of functioning in *E.coli* or *S.cerevisiae* as well as genetic makers which allow for selection and maintenance of plasmid transformed cells in *E.coli* (by Ampicillin resistance) or suitable strains of *S.cerevisiae* (in which the LEU2 gene allows transformed leu2 recipients to grow in the absence of leucine). It is recognized, however, that plasmids equivalent to pUTX37 or any other DNA sequence capable of introduction, replication (whether autonomous replication or replication by integration into at least one of the yeast chromosomes), and selection in a host yeast microorganism may be sufficiently utilized as a transfer vector in the present invention.

Figure 4A:
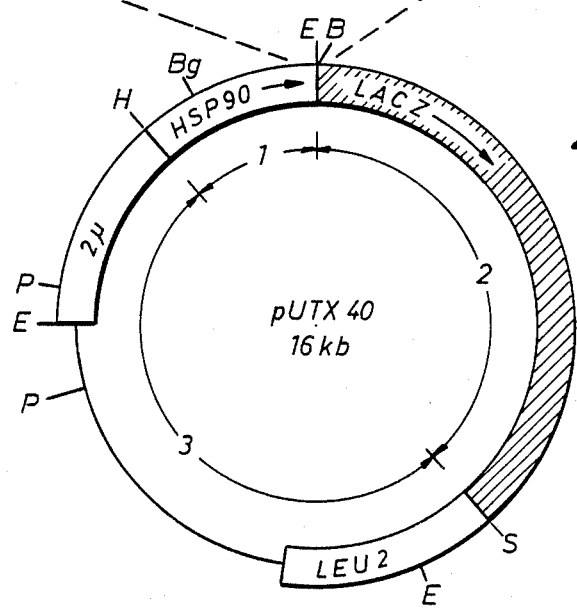
FIG. 4A shows the recombinant transfer vector pUTX40 produced by combining the 1.875 kilobase pair Hind III-Eco RI segment of pUTX1 (FIG. 2B) with the 6.2 kilobase pair Eco RI-Sal I fragment of pMC1403 (FIG. 3) and the 8.0 kb Hind III-Sal I fragment of pUTX37 (FIG. 1). The Hind III - Bam HI fragment is a combination of the Bam HI - Sal I fragment (designated as region -2- in the the drawing) and the adjacent Sal I - Hind III fragment (designated as region -3- in the drawing). The Hind III Bam HI fragment is approximately 14.1 kilobase pairs in length. The size of this recombinant vector is 16 kilobase pairs.

In accordance with the present invention, the Eco RI end of the 1.875 kilobase Hind III - Eco RI fragment comprising the HSP90 gene is ligated to the Eco RI site of the 6.2 kilobase Eco RI - Sal I fragment comprising the lac Z gene in the presence of the above described fragment of pUTX37. The desired combination of the three DNA fragments (directed by each of the differing cohesive termini) is achieved by the ligation with the enzyme T4 ligase in accordance with standard recombinant procedures to produce plasmid pUTX40. (See FIG. 4A).

It should be noted that fusion of the DNA fragments described above to produce pUTX40 is carried out to include the regulatory sequence and at least a segment of the coding sequences of the HSP90 gene. Further, fusion is carried out such that the point of fusion is located within the coding sequences of the HSP90 gene and within or adjacent to the coding sequence of the lac Z gene. Accordingly, the resultant gene product of pUTX40 will be a fused protein, however, it will not be an enzymatically active fused protein as the translational reading frames are incompatible at the point of fusion.

Figure 4B:
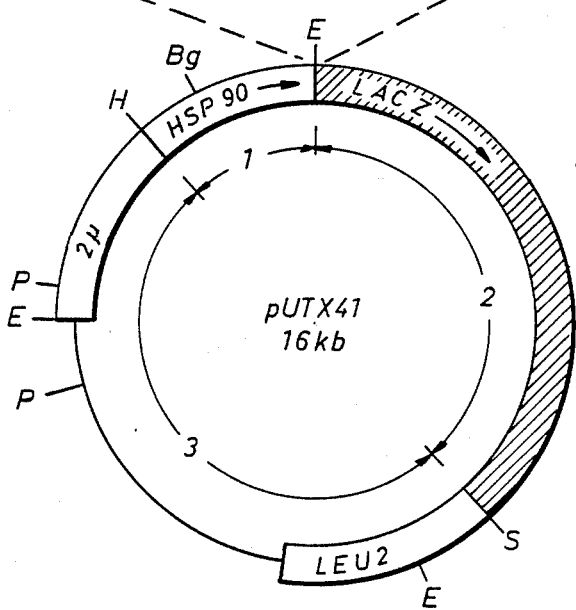
FIG. 4B shows the 16 kilobase pair recombinant transfer vector pUTX41 which is produced by cutting plasmid pUTX40 at its unique Bam HI site, filling the cohesive ends, and reclosing the plasmid. The detail indicates the reading frame modification which has brought the lacZ gene into the appropriate orientation to produce a functionl fused protein.

The preferred recombinant transfer vector, pUTX41, comprising the material to be incorporated into a host yeast, is generated from pUTX40 by cutting the plasmid at its unique Bam HI restriction site, filling cohesive termini, and rejoining the plasmid. This manipulation renders the translational reading frames compatible across the fusion point such that the resultant gene product of pUTX41 will be an enzymatically active fused β-galactosidase molecule. (See FIG. 4B). Further, the amino terminus of this fused protein will consist of a portion of the hsp90 protein and the carboxyl terminus will consist of the lac Z protein (β-galactosidase). Alternatively, fusion may be carried out to include the regulatory sequence of HSP90, but not the DNA sequences encoding for the hsp90 protein such that the resultant gene product will be β-galactosidase. Additionally, it is recognized that recombinant transfer vectors equivalent to plasmid pUTX41 may also be suitably utilized in the present invention provided the heat shock inducible gene region of an appropriate yeast microorganism is functionally incorporated into the recombinant transfer vector.

The desired genetic material is thereafter introduced into S.cerevisiae DC5, the preferred host yeast microorganism, by the process of transformation. The preferred means of accomplishing transformation is essentially as described by Beggs, "Transformation of Yeast by Replication Hybrid Plasmid" Nature 275:104–109 (1978). However, it is recognized that transformation may be accomplished by a number of procedures equivalent to the preferred means. The transformed host, S.cerevisae DC5/pUTX41 was deposited on April 22, 1983 with the Agricultural Research Service Culture Collection, Northern Regional Research, Peoria, Ill. (NRRL #Y-15408).

The transformed host yeast is thereafter cultured in an appropriate medium permitting only the growth of transformed microorganisms. In the case of pUTX41, which carries the LEU2 gene, transformation of S.cerevisiae DC5 (which contains a mutant leu2 gene) confers the ability for leucine independent growth upon the host yeast microorganism. Accordingly, strains of transformed S.cerevisiae DC5 microorganisms capable of the heat-regulated synthesis of selected and fused proteins, are selected. However, it is recognized that other suitable hosts and other suitable genetic markers providing selection of transformants by complementation or other selection procedures may be utilized in the present invention.

Heat-regulated synthesis of β-galactosidase or a fused protein having β-galactosidase activity is made possible by the gene fusion of the lacZ gene of E. coli to the HSP90 gene under heat shock control. Expression of the fused gene in yeast may be "turned on" by elevation of the cultivation temperature of the microorganism either by a transient increase from 23° to 36° or by a continuous shift in temperature from 23° to 36°. Therefore, by this mechanism, one may control the point in cultivation where β-galactosidase or a fused protein having β-galactosidase activity is synthesized merely by temperature control of the fermentation culture. Additionally, the fusion of the lacZ gene to the HSP90 regulatory sequence allows a level of production of β-galactosidase or the fused protein in yeast consistent with the high level of synthesis of the hsp90 protein when the HSP90 gene is induced.

MATERIALS AND METHODS

Host Yeast

The host used in the examples, S.cerevisiae strain DC5, was obtained from Dr. Michael G. Douglas, University of Texas Health Science Center, San Antonio, Tex.

Yeast DNA

The yeast DNA used in the examples, comprising the HSP90 gene of S.cerevisiae, was isolated and selected from the recombinant libraries, λCharon 4-S.cerevisiae and YEp13 - S.cerevisiae, obtained from Dr. Richard Kramer, Hoffman La-Roche, Inc., Nurtley, N.J., and Dr. Michael S. Douglas, University of Texas Health Science Center, San Antonio, Tex., respectively.

The phages and plasmids used in the examples are as follows:

λCharon 4-S.cerevisiae Library

Recombinant library of partial Eco RI digest of S. cerevisiae DNA (strain S288c) inserted into λcharon 4.

λYhsil

Recombinant phage isolated from λcharon 4-S.cerevisiae library which contains the yeast HSP90 gene as a part of a 15.16 kilobase insert of S.cerevisiae DNA in λcharon 4.

YEp13-S.cerevisiae Library

Recombinant library of partial Sau 3A digest of S. cerevisiae DNA (strain AB320) inserted into the Bam Hl site of YEp13. This library is fully described in Nasmyth, K.A. and Tatchell, K., Cell 19:753 (1980).

pYhsil

Recombinant plasmid isolated from YEp13-S.cerevisiae library which contains the yeast HSP90 gene as a part of a 9.2 kilobase insert of S.cerevisiae DNA in YEp13.

pUTX1

Subclone of 1.875 kilobase Hind III EcoRI fragment of S. cerevisiae DNA insert from pYhsil inserted between Hind III and EcoRI sites of pBR322. This Hind III-EcoRI fragment contains the HSP90 regulatory sequence as well as the coding sequences for the first 516 amino acid residues of hsp90 protein.

pUTX37

Transfer vector which contains a segment of the yeast plasmid 2μ DNA, and the yeast LEU2 gene.

E. coli DNA

The DNA used in the examples, comprising the lacZ gepe of E.coli, was isolated from the plasmid pMC1403, obtained from Dr. Malcolm Casadaban, University of Chicago, Chicago, Ill.

DNA Comprising HSP90-lacZ Fusion pUTX40

Out of frame HSP90 - lacZ fusion.

pUTX41

In frame HSP90 - lacZ fusion.

Yeast Transformation, Growth, Labeling and Protein Analysis

S.cerevisiae strain DC5 (MATa, leu2-3, leu2-112, his3, canl-11) was used as a transformation recipient for LEU2 bearing plasmids. See, Beggs, J. P. "Transformation of Yeast by a Replicating Hybrid Plasmid," *Nature* 275:104 (1978). Transformants were selected and maintained on a defined nutritionally selective medium using 2% glucose as a carbon source. See, Finkelstein, D.B. and Strausberg, S. "Identification of Expression of a Cloned Yeast Heat Shock Gene," *J. Biol. Chem.* 258:1908 (1983). Growth, heat shocking, pulse labeling with 35 S-methionine, preparation of SDS-soluble proteins, gel electrophoresis, staining and autoradiography were performed as described in McAlister, L. et al., "Altered Patterns of Protein Synthesis, Induced by Heat Shock of Yeast," *Curr. Genet.* 1:63 (1979). For the isolation of SDS-soluble proteins from cells grown on plates, colonies were transferred to water with a toothpick to give a concentration of $2 \times 10^7$ cells/ml and protein isolation was carried out exactly as described in McAlister, L. et al., "Altered Patterns of Protein Synthesis Induced by Heat Shock of Yeast," *Curr. Genet.* 1:63 (1979). Stained gels were scanned at 625 nm using a Transidyne 2955 Scanning Densitometer.

E.coli Growth, Transformation, and Plasmid Isolation

Growth and transformation of E.coli K12 strain MC1066 (leuB-600), lacIPOZY), ΔX74, trpC-9830, strA, pyrF74::Tn5) were accomplished by cultivation at 370° C. in L broth as described in Holland et al., *Methods Enzymol* 68, 408 (1979), or in M-9 minimal medium, Miller, "Experiments in Molecular Gentics," Cold Spring Harbor Laboratory, Cold Spring Harbor, N.Y. (1972). Plasmids were isolated or described in Finkelstein, D. B. and Strausberg, S., "Identification and expression of a cloned yeast heat shock gene," *J. Biol. Chem.* 258:1908 (1983).

EXAMPLE I

CONSTRUCTION OF THE RECOMBINANT VECTOR pUTX41

The recombinant vector pUTX41 which expresses a fused protein having β-galactosidase activity in yeast was constructed as follows:

STEP A. Isolation of Yeast HSP90 gene

A recombinant library containing yeast DNA of S.cerevisiae strain S288C partially digested with restriction enzyme Eco R1 and inserted into the vector charon 4-S.cerevisiae recombinant library was grown on the E.coli host strain K802. Identification of recombinant phage containing heat shock inducible genes was accomplished by differential hybridization analysis using in vivo 32p pulse-labeled yeast polyA RNA of S.cerevisiae. Labelling, purification and hybridization were performed as described in Finkelstein, D. B. et al., "Alterations of Transcription During Heat Shock of Saccharomyces Cerevisiae", *J. Biol. Chem.* 257:8405 (1982), which is herein incorporaeed by reference. Phage which showed a more intense hybridization to the in vivo labelled RNA isolated from S. cerevisiae during heat shock than to the in vivo labelled RNA isolated from S. cerevisiae prior to heat shock were purified and evaluated. Purification and evaluation of yeast DNA sequences was accomplished by the ability of the yeast DNA sequences to hybrid-select yeast RNA molecules which upon in vitro translation by reticulocyte lysate extracts directed the synthesis of polypeptide products which comigrated with authentic yeast heat shock proteins when examined by SDS-polyacrylamide gel electrophoresis. See, Finkelstein, D. B. et al., "Alterations of Transcription During Heat Shock of Saccharomyces Cerevisiae", *J. Biol. Chem.* 257:8405 (1982), which is herein incorporated by reference. A recombinant phage containing the HSP90 gene region, designated as λYhsil and characterized as a recombinant λcharon 4 phage containing a 15.16 kilobase segment of S.cerevisiae including the HSP90 gene region, was nick-translated with $[\alpha-^{32}P]ATP$. This labelled DNA was used as a hybridization probe in screening the recombinant plasmid DNA library YEp13-S. cerevisiae. This recombinant library was thereafter introduced into E. coli strain RR1 by transformation and screened with the labelled λYhsil. See, Finkelstein, D. B. and Strausberg, S., "Identification and Expression of a Cloned Yeast Heat Shock Gene," *J. Biol. Chem.*, 258:1908 (1983). The cells containing plasmid which hybridized to this labelled probe were subcloned and plasmid was purified from these cells and examined by agarose gel electrophoresis after digestion with restriction enzymes Eco R1 or Hind III for the presence of 3.45 kilobase and 2.95 kilobase Eco R1 fragments and for a 5.6 kb Hind III fragment of DNA. The plasmid containing these features, designated pYhsil, was isolated from E coli and introduced into S. cerevisiae strain DC5 by transformation as described in Beggs, J. B. *Nature* 275:104 (1978). Transformed yeast were selected by their ability to grow in the absence of added leucine. The pYhsil-transformed S.cerevisiae were grown in liquid culture at 23° C. in a growth medium consisting of 0.67%. Bacto yeast nitrogen base without amino acids, 2% glucose and 20 μg/ml histidine (or other equivalent growth media lacking leucine) and pulse labelled by administration of $35_S$ methionine for 15 min at a time starting 15 min after the culture had been shifted to 36° C. Cultures were harvested, SDS-soluble proteins were extracted and evaluated by SDS polyacrylamide gel electrophoresis and autoradiography. Confirmation of the presence of the intact HSP90 gene region on plasmid pYhsil was obtained by an excess amount of the hsp90 protein relative to that observed in YEp13-transformed S. cerevisiae strain DC5 treated under identical conditions.

STEP B. Construction of pUTX1

Plasmid pYhsil was isolated from the above described transformed E. coli, and digested with Eco RI and Hind III, restriction enzymes. The desired DNA fragment of 1.85 kilobases, which contains the DNA sequences regulating expression as well as a portion of the sequence encoding the hsp90 protein, was mixed with plasmid pBR322 which had been cut with the restriction enzymes Eco RI and Hind III. Specifically, 5 μg of pYhsil and 5 μg of pBR322 were separately digested to completion with Hind III and Eco RI. The 1.85 kilobase fragment was purified and mixed with pBR322, ligated at 14° C. for 16 hours in a volume of 60 μl in buffer 50 mMTris-Cl (pH7.4), 10 mM $MgCl_2$, 10mM dithiothreitol, and 1 mM ATP in the presence of 400 units of T4 DNA ligase (New England Biolabs). The ligation mix was ethenol-precipitated and resuspended in the presence of 100 μl of 0.01 M Tris-Cl, 0.001 m EDTA (pH7.4) and 5 μl were used to transform E.coli strain MC1066. Transformed E. coli were selected by their ability to grow in the presence of 25 μg/ml of ampicillin. Transformants which contained the appropriately joined DNA fragments, designated plasmid pUTX1, were further identified by their inability to grow on growth medium in the presence of 10 μg/ml tetracycline. The structure of the plasmid pUTX1 when isolated from these transformed cells was confirmed by digestion with the restriction enzymes Eco RI and Hind III.

STEP C. Construction of pUTX40

For the construction of the out-of-frame HSP90-lacZ gene fusion (pUTX40), the appropriate fragments were purified by agarose gel electrophoresis prior to ligation. 2.5 μg of pUTX1 (containing the 3' deleted HSP90 gene consisting of the regulatory sequence of HSP90 as well as the sequences encoding the first 516 amino acid residues of the hsp90 protein), pMC1403 (containing the 5' deleted lacZ gene consisting of the sequences encoding all but the first 8 amino acid residues of β-galactosidase) and pUTX37 (containing both yeast and *E. coli* selectable markers and replication origins) were digested with Hind III plus Eco RI, Eco RI plus Sal I, and Hind III plus Sal I, respectively. The appropriate purified fragments were mixed and ligated in a volume of 60 μl of 50 mM Tris-Cl (pH 7.4), 10 mM MgC12, 10 mM dithiotheritol and 1 mM ATP in the presence of 1 μl of T4 DNA ligase (New England Biolabs) for 16 hours at 14° C. *E. coli* MC1066 was transformed with 3 μl of the ligation mixture and spread on XGal plates containing ampicillin. After 5 days of incubation at 37° C. approximately 50% of the colonies showed a very faint greenish color. The plasmids isolated from most of these colored colonies were identical, and one was designated pUTX40.

STEP D. Construction of pUTX41

Plasmid pUTX41 was constucted by filling in the cohesive termini 1 μg of BamHI cleaved pUTX40 in an incubation (50 μl of 50 mM Tris-Cl [pH 7.8], 5 mM MgCl$_2$, 10 mM β-mercaptoethanol and 20 mM each of dATP, dGTP, dCTP and dTTP) containing 5 units of *E. coli* DNA polymerase I (large fragment, New England Biolabs) for 30 min at room temperature. Following ethanol precipitation, the DNA was recircularized by incubation for 16 hours at 14° C. in 60 μl of the buffer used for cohesive end ligation as described above in the presence of 3 μl T4 DNA ligase. After a further digestion with BamHI (to reduce the background of plasmids with an unfilled BamHI site) the entire mixture was used to transform *E. coli* MC1066 Approximately 10% of the transformants (plated on XGal plates containing ampicillin) showed a blue color within 24 to 36 hours of growth at 37° C. Plasmids isolated from a number of these blue colonies had a restriction map identical to that of pUTX40 with the exception of the absence of a BamHI cleavage site.

EXAMPLE 2

Transformation of *S.cerevisiae* Strain DC5

Transformation of *S.cerevisiae* DC5 was performed essentially as described by Beggs, J. P. "Transformation of yeast by a replicating hybrid plasmid," *Nature* 275:104 (1978), which is herein incorporated by reference.

Cells cultivated at 23°–30° in 1% yeast extract, 2% peptone, 2% dextrose to a density of $1 \times 10^8$ cells/ml were harvested, washed, and resuspended to a density of $5 \times 10^8$ cells/ml in 1.2 M sorbitol. Cells were converted to spheroplasts by incubation for 15–20 min with zymolase 60,000 (200 μg/ml). Spheroplasts were washed twice by centrifugation and resuspension in 1.2 M sorbitol and washed one time further with 1.2 M sorbitol, 0.01 M CaCl$_2$, 0.01 M Tris Cl pH 7.4 (solution A). Spheroplasts were centrifuged and resuspended to a density of $10^{10}$ spheroplasts/ml. Aliquots of 0.1 ml were transferred to sterile tubes. Plasmid pUTX41 (1–10 μg in a volume of 100 μl of solution A) was added to the spheroplasts and the mixture allowed to incubate for 15 minutes at which time 0.9 ml of solution B (20% [w/v] polyethylene glycol 4000, 0.01 M CaCl$_2$, 0.01 M Tris-Cl pH 7.4) was added and the mixture was allowed to incubate for a further 15 min. The mixture was centrifuged and the pellet resuspended in 150 μl of solution C (1.2 M sorbitol, 6.7 mM CaCl$_2$, 0.33% yeast extract, 0.67% peptone, 0.67% dextrose) and incubation continued for 20 min.

The mixture was diluted to 1.0 ml with 1.2 M sorbitol and 200 μl aliquots plated by the "pour plate" procedure in regeneration agar. Regeneration agar is 0.67% yeast nitrogen base (without amino acids), 2% dextrose, 30 μl g/ml histidine, 1.2 M sorbitol and 3% agar.

This media allows growth of transformed cells only by selecting for leucine independent growth which is provided by plasmid complementation of the chromosomal leu2 defect of *S. cerevisiae* DC5.

EXAMPLE 3

Analysis of Protein Synthesized by Transformed Yeast

Yeast transformed with plasmid pUTX41 were grown to a density of $2 \times 10^7$ cells/ml at 23° C. in liquid medium containing 0.67% yeast nitrogen base (without amino acids), 2% dextrose and 30 μg/ml histidine. A portion of each culture was shifted to 36° (to elicit the heat shock response) and incubation of both shifted and unshifted culture continued for 2 hours. To assay for β-galactosidase activity 20 μl of each culture was added to 1 ml of Z buffer (0.06 M Na$_2$HPO$_4$, 0.04 M NaH$_2$PO$_4$, 0.01 M KCl, 0.001 M MgSO$_4$, 0.05 M β-mercaptoethanol, pH 7.0) which contained 20μl of 0.1% sodium dodecyl sulfate and 50 μl of CHCl$_3$. The mixture was vortexed for 30 sec and then placed in a 28° water bath for 5 min. β-galactosidase activity was measured by the hydrolysis of ONPG (o-nitrophenol phenol β-D galactose). The reaction was started with the addition of 200 μl of an aqueous solution containing 4 mg/ml ONPG. Incubation was carried out for 10 minutes. The reaction was terminated by the addition of 0.5 ml of 1 M Na$_2$CO$_2$. The hydrolyzed product was determined spectrophotometrically at 420 nm. Activity is expressed as nmol o-nitrophenol-β-D-galactoside hydrolyzed per min per mg protein. $A_{420}=0.0045$ represents 1 nmole o-nitro-phenol. Protein content was related to turbidity where 1 Klett unit of yeast cells (Klett Summerson colorimeter, 660 nm filter)=2 μg protein.

| β-Galactosidase Activity in pUTX41-Transformed Yeast | | |
|---|---|---|
| | Enzyme Activity (Units/mg protein) | |
| | Average | Range |
| Unshifted Temperature | 4400 ± 550 | (3119–5765) |
| Shifted to 36° C. for 2 hrs. | 8900 ± 960 | (6700–11,161) |

These values represent assays performed on five independently isolated transformants. An enzyme activity of 3,000 U/mg protein represents 1% of the total cell protein of the yeast.

EXAMPLE 4

Construction of a Recombinant Vector Which Expresses β-Galactosidase in Yeast A vector which expresses β-galactosidase in yeast would be constructed as follows:

Five micrograms of the plasmid pUTX1 are digested with the enzyme HinfI and the 0.896 kilobase fragment which contains the HSP90 promoter as well as a portion of the 5' untranslated gene region is purified by gel electrophoresis. The cohesive ends of the fragment are made flush by incubation in a volume of 50 μl of 50 mM Tris-Cl (pH 7.8), 5 mM $MgCl_2$, 10 β-mercaptoethanol, 20 mM each of dATP, dGTP, dCTP and dTTP, 5 units of E. coli DNA polymerase I (large fragment) for 30 min at room temperature. The filled in fragment is ethanol precipitated and resuspended in a volume of 10 μl of buffer D (buffer D is 50 mM Tris-Cl [pH 7.4], 10 mM $MgCl_2$, 10 mM dithiothreitol, 1 mM ATP) and added to 2 μg of phosphorylated Cla linkers (3.5 μg of Cla linkers, CATCGATG, are phosphorylated by incubation in 20 μl of 70 mM Tris-Cl [pH 7.6], 10 mM $MgCl_2$, 5 mM dithiothreitol, 1 mM ATP and 4 μl of T4 polynucleotide kinase at 37° for 30 min. The reaction mixture is extracted 20 μl $CHCl_3$ and residual organc solvent removed with a stream of $N_2$) in a total volume of 40 μl of buffer D containing 4 μl of T4 DNA ligase and incubated at 14° C. for 16 hours. Following this incubation the reaction mixture is ethanol precipitated and resuspended in a volume of 400 μl and digested with the restriction enzyme ClaI (100 U) for 16 hours at 37° C. and reprecipitated with ethanol. The resulting fragment, containing filled in HinfI sites and having ClaI-generated cohesive termini is purified by gel electrophoresis.

Plasmid pBR322 (1 μg) is linearized by digestion with the restriction enzyme BamHI. The cohesive ends are filled, Cla linkers added, the resulting DNA digested with ClaI and gel purified (exactly as described above for the HinfI generated fragment).

The fragments are resuspended in a total volume of 30 μl of buffer D containing 2 μl T4 DNA ligase and the joined together by incubating at 14° C. for 16 hours. Ten microliter aliquots of the ligation mixture are used to transform E. coli strain MC1066. Transformants are selected by the phenotype of ampicillin resistance and screened for the presence of the desired plasmid designated as pUTX1000t.

Cells bearing pUTX1000t are grown and plasmid pUTX1000t is prepared. Two and one half micrograms of pUTX1000t is digested with the restriction enzymes HindIII and BamHI and the 0.201 kilobase fragment is purified by gel electrophoresis. Two and one half micrograms of the plasmid pUTX40 are digested with HindIII and BamHI and the 14.1 kilobase pair fragment is purified by gel electrophoresis. The Hind III-BamHI fragments of pUTX1000t and pUTX40, respectively, are combined in a volume of 60 μl of buffer D containing 1μl of T4 DNA ligase and joined by incubation for 16 hours at 14° C. Ten microliter aliquots of this ligation mixture are used to transform E. coli strain MC1066 and transformants selected by the phenotype of ampicillin resistance and screened for the presence of a plasmid designated pUTX1001t. The plasmid pUTX1001t contains no sequences which encode the hsp90 protein and has introduced the sequence ATG (the start codon for lacZ expression) in the appropriate reading frame to allow the heat regulated expression of β-galactosidase (containing no other protein sequence) in yeast. This may be confirmed by introducing plasmid pUTX1001t into S. cerevisiae strain DC5 by transformation (as in Example 2) and assaying for heat regulated expression of β-galactosidase (as in Example 3).

The foregoing description has been directed to particular embodiments of the invention in accordance with the requirements of the Patent Statutes for the purposes of illustration and explanation. It will be apparent, however, to those skilled in the art that many modifications and changes will be possible without departing from the spirit and scope of the invention. It is intended that the following claims be interpreted to embrace all such modifications and changes.

What is claimed is:

1. A process for producing a transformed S. cerevisiae yeast microorganism capable of heat regulated synthesis of a selected unfused protein, which comprises:
    (1) cleaving DNA having a heat shock inducible gene of a S. cerevisiae yeast microorganism to produce a promoter sequence of said heat shock inducible gene and excluding the structural gene sequence coding for the heat shock protein;
    (2) preparing a recombinant transfer vector by combining a suitable transfer vector with said promoter sequence obtained in step (1) and a DNA fragment comprising a DNA sequence encoding for said selected heterologous protein, said transfer vector being capable of replication in a host yeast microorganism, said promoter sequence and said DNA fragment being capable of recombination;
    (3) transforming said host yeast microrogansim with said recombinant transfer vector;
    (4) culturing said transformed host yeast microorganism; and
    (5) selecting a transformed host microorganism capable of heat regulated synthesis of said selected unfused heterologous protein.

2. The process of claim 1 wherein said heat shock inducible gene is HSP90.

3. The process of claim 1 wherein said DNA fragment comprises a lacZ gene of E. coli.

4. The process of claim 1 wherein said transfer vector is derived from a plasmid DNA.

5. The process of claim 4 wherein said plasmid DNA is pUTX37.

6. The process of claim 1, wherein said promoter sequence is further defined as a 0.201 kilobase pair Hind III - Bam HI DNA fragment from the Heat Shock promoter region of S. cerevisiae HSP90.

7. A transformed S. cerevisiae yeast microorganism, capable of heat regulated synthesis of a selected unfused heterologous protein, containing therein a plasmid or other DNA sequence capable of replication in said yeast microorganism and comprising the combination of a promoter sequence of S. cerevisiae heat shock inducible gene excluding the structural gene sequence coding for the heat shock protein, and a second DNA fragment having a DNA sequence encoding for said selected protein.

8. The transformed microorganism of claim 7 wherein said heat shock iducible gene is HSP90.

9. The transformed microroganism of claim 7 wherein said second DNA fragment comprises a lacZ gene of *E. coli*.

10. The transfromed yeast microorganism of claim 7, wherein said promoter sequence is further defined as a 0.201 kilobase pair Hind III - Bam HI DNA fragment from the Heat Shock promoter region of *S. cerevisiase* HSP90.

11. A process for heat regulated synthesis of a selected unfused heterologous protein within a transformed *S. cerevisiae* yeast microroganism, which comprises culturing said yeast microorganism, said microorganism having been transformed with a recombinant transfer vector comprising the combination of a prmomoter sequence of a *S. cerevisiae* heat shock inducible gene excluding the structral gene sequence coding for the heat shock protein, and a second DNA fragment having a DNA sequence encoding for said selected protein.

12. The process of claim 11 wherein said heat shock inducible gene is HSP90.

13. The process of claim 11 wherein said second dNA fragment comprises a lacZ gene of *E. coli*.

14. The process of claim 11, wherein said prpomoter sequence is further defined as a 0.201 kilobase pair Hind III - Bam HI DNA fragment from the Heat Shock promoter region of *S. cerevisiae* HSP90.

15. The transformed microorganism *S. cerevisiae* DC5/pUTX41.

* * * * *